(12) United States Patent
Tropp

(10) Patent No.: US 7,250,764 B2
(45) Date of Patent: Jul. 31, 2007

(54) SHIELDED DOME RESONATOR FOR MR SCANNING OF A CEREBRUM

(75) Inventor: James S. Tropp, Berkeley, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 831 days.

(21) Appl. No.: 10/605,184

(22) Filed: Sep. 12, 2003

(65) Prior Publication Data
US 2005/0059882 A1    Mar. 17, 2005

(51) Int. Cl.
G01V 3/00    (2006.01)

(52) U.S. Cl. .................... 324/318; 324/309

(58) Field of Classification Search ............ 324/318, 324/319, 322, 309, 307, 300; 600/410, 320, 600/422, 445
See application file for complete search history.

(56) References Cited

U.S. PATENT DOCUMENTS

| | | | |
|---|---|---|---|
| 5,515,855 A | 5/1996 | Meyer et al. | |
| 5,602,479 A | 2/1997 | Srinivasan et al. | |
| 5,682,893 A | 11/1997 | Meyer et al. | |
| 6,029,082 A * | 2/2000 | Srinivasan et al. | 600/422 |
| 6,452,393 B1 | 9/2002 | Allen et al. | |
| 6,591,128 B1 * | 7/2003 | Wu et al. | 600/422 |
| 6,710,598 B2 * | 3/2004 | Leussler et al. | 324/318 |
| 7,084,630 B2 * | 8/2006 | Ludwig et al. | 324/318 |

* cited by examiner

Primary Examiner—Brij Shrivastav

(57) ABSTRACT

A dome resonator (11) includes a resonator circuit (70) that excites and/or receives radio frequency magnetic resonance signals that emanate from a region of interest (14). The resonator circuit (70) includes multiple longitudinal conductive elements (110) that are coupled at a first end (80) and a second end (82) and tapered from the first end (80) to the second end (82). A resonator circuit support (74) is coupled to and supports the resonator circuit (70). A shield (76) is coupled to the resonator circuit support (74) and electrically isolates the resonator circuit (70) from a surrounding environment.

21 Claims, 6 Drawing Sheets

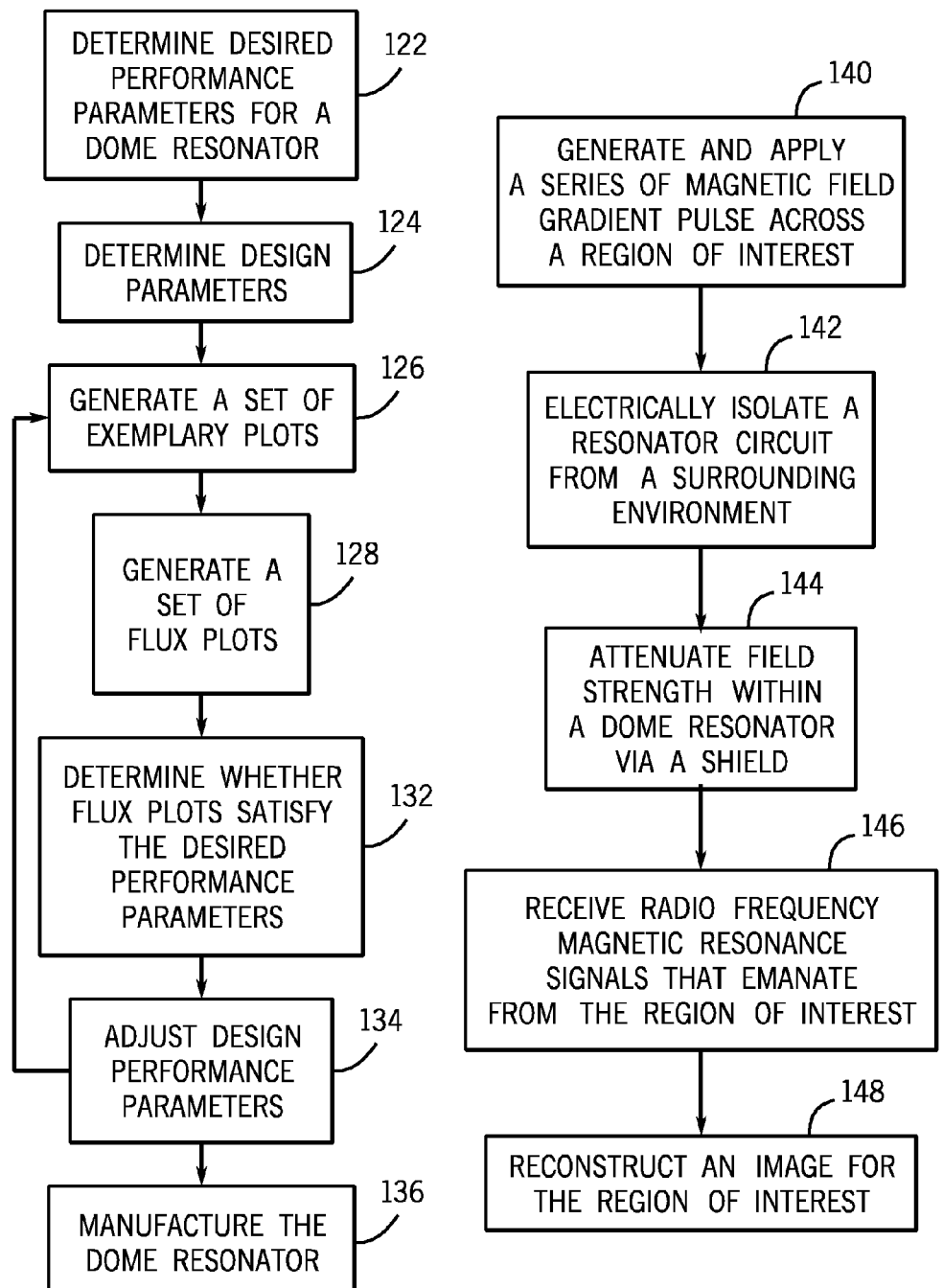

SHIELDED DOME RESONATOR FOR MR SCANNING OF A CEREBRUM

BACKGROUND OF INVENTION

The present invention relates generally to neurological magnetic resonance (MR) imaging systems, and more particularly, to an apparatus and system for MR scanning and imaging of a cerebrum.

In neurological magnetic resonance imaging, a patient is typically positioned within a strong, temporally constant magnetic field. A time series of magnetic field gradient pulses, for encoding spatial location, are applied across a region of interest within the magnetic field. Concurrently, radio frequency pulses are applied for inducing and manipulating magnetic resonance of dipoles in the region of interest. A system of radio frequency transmitting and receiving coils is positioned over the head and neck portions of a patient to excite and receive radio frequency magnetic resonance signals within the region of interest.

Several types of radio frequency coils are utilized in the art, including coils of a "Birdcage Resonator" type, of a Transverse Electromagnetic (TEM) type, and of a "Dome Resonator" type. Each of these resonators, when suitably configured, can act as a transmitter and/or receiver for exciting and/or receiving magnetic resonance within a selected volume of interest, as is known in the art.

Coils of the birdcage resonator type are typically in the form of a ladder circuit, which may be of high pass or low pass type. The ladder circuit is typically of cylindrical form and has axially-directed runners extending between a pair of coaxial conductive rings, sometimes referred to as "end rings", located at the peripheries of the cylinder, and extending azimuthally thereabout. In the low pass birdcage type, each runner has a given number of capacitors; in the high pass birdcage type, each ring segment joins two runners and has a given number of capacitors.

A birdcage coil may or may not be fitted with a cylindrical conductive shield, surrounding, but typically not touching, the resonant structure; the stand off distance between shield and resonator is a design variable. The function of the shield is twofold: i) to reduce electromagnetic couplings to surrounding conductive objects, which are harmful since they can detune the resonator or constitute an extraneous source of energy losses, and ii) to cancel or reduce radiative losses from the resonator at sufficiently high frequencies. The benefits of shielding are typically realized in resonators operating at rather high radio frequencies that are often above 100 MHz.

TEM coils are similar to coils of the shielded birdcage type, in that they are cylindrical, and have axially directed longitudinal runners; but these runners are not conductively connected to end rings. Instead, the runners are connected to the outer cylindrical shield via distributed or discrete capacitance. Inasmuch as the runners themselves constitute typically an inductive impedance, the circuit of each runner is connected capacitively to the shield and may be viewed as a low pass pi circuit over a ground plane.

Standard geometry of a coil of the shielded birdcage resonator type and of the TEM type provide a uniform RF B field, but can be claustrophobic in nature and are inefficient for imaging of just a cerebrum, since they bound a relatively large volume as compared to coils of the dome resonator type, which contain comparatively less tissue. That is, since the principle loss mechanism in imaging resonators is from radiofrequency eddy currents, due to the conductivity of the specimen being imaged, lowering the amount of tissue within the resonator also lowers the losses and leads to a more efficient resonator.

The birdcage and the TEM coils are inefficient due to their large size, which can cover a larger portion of a patient than is usually of interest. Also, the birdcage and the TEM coils experience greater than necessary power dissipation and usually acquire data from regions of a body that are not necessarily of interest.

The dome resonator coil has not achieved wide usage and is defined as a radio frequency (RF) resonator that includes conductors and capacitors arrayed upon an outer surface of a hollow dome-shaped lamina, such as commonly referred to as a surface of revolution, for example a paraboloid. The dome resonator is usually employed for its high sensitivity, despite its poor RF homogeneity, which has tended to restrict its use to pure reception as opposed to being used for transmission. Similar to the birdcage coil design, the dome resonator coil includes longitudinal runners that extend between an aperture ring and an apex. Each runner, such as in a low-pass dome resonator type, has a given number of capacitors.

The dome resonator coil is intended typically, though not exclusively, to serve as an antenna for MR imaging and spectroscopy of a human cerebrum or brain. The hollow dome shape of the dome resonator coil is designed so that its interior bounds a volume approximating the shape of a human head, which is intended to fit therein.

Coils of the dome resonator type are streamlined, patient friendly, and efficient, but produce a non-uniform RF B field. The non-uniform B field increases in strength closer to the apex, due to bunching or close proximity of the conductive runners and concomitant bunching of magnetic flux lines. The increase in field strength near the apex causes the field to be non-uniform and thus degrades image quality.

In addition to the above stated and associated disadvantages of the existing RF coil devices, the RF resonators are, as noted above, more and more likely to be subject to parasitic electromagnetic couplings to surrounding metallic objects as well as to radiation losses. This is especially true when MR imaging and spectroscopy systems operate at increased static field strengths and use higher frequencies.

It is desirable to operate within increased static field strengths, such as 3.0 T and 4.0 T, instead of the conventional 1.5 T. Unfortunately, due to electrical properties of a patient, artifacts are increased at the higher static field strengths. However, rapid pulsing and non-zero relaxation rates tend to mitigate these artifacts and produce a leveled image, provided that the distortion is not originally overly severe. The artifacts derive from the fact that a human head has electrical properties such that it is a lossy ellipsoid of high dielectric constant, which produces resonant effects at radio frequencies required for performance of MR imaging and spectroscopy at static fields above 3.0 tesla. The resonant effects distort uniformity of the RF excitation. The result is the production of artifacts in the form of distorted image intensities, which are typically brightened at the centers of the images.

It is therefore desirable to provide an RF receiving coil device that has the advantages of both the birdcage/TEM type coils and the dome resonator type coil without the above-stated disadvantages and at the same time is less susceptible to higher frequencies and static field strengths.

SUMMARY OF INVENTION

The present invention provides an apparatus and system for MR scanning and imaging of a cerebrum. A dome resonator is provided that includes a resonator circuit that excites and/or receives radio frequency magnetic resonance signals that emanate from a region of interest. The resonator circuit includes multiple longitudinal conductive elements that are coupled at a first end and a second end and tapered from the first end to the second end. A resonator circuit support is coupled to and supports the resonator circuit. A shield is coupled to the resonator circuit support and electrically isolates the resonator circuit from a surrounding environment.

One of several advantages of the present invention is that it provides a dome resonator that is capable of performing high field magnetic resonance imaging and spectroscopy studies of a cerebrum with improved sensitivity and electrical isolation.

Another pair of advantages of the present invention is that in being dome shaped provides both patient comfort and imaging efficiency.

Furthermore, the present invention provides a dome resonator that is shielded, which prevents parasitic coupling to the surroundings, and therefore consequently prevents detuning of the resonator circuit and extraneous electrical losses.

Moreover, the present invention provides a dome resonator configuration such that distance between the shield and the resonator circuit decreases towards an apex of the dome resonator. In so doing, the present invention increases attenuation of field of the resonator near the apex where field strength is typically highest, thus providing a uniform field within the dome resonator. In providing a uniform field image quality is increased.

The present invention itself, together with attendant advantages, will be best understood by reference to the following detailed description, taken in conjunction with the accompanying figures.

BRIEF DESCRIPTION OF DRAWINGS

For a more complete understanding of this invention reference should now be had to the embodiments illustrated in greater detail in the accompanying figures and described below by way of examples of the invention wherein:

FIG. 5 is a logic flow diagram illustrating a method of designing and manufacturing a dome resonator in accordance with an embodiment of the present invention.

FIG. 7 is a logic flow diagram illustrating a method of method of reconstructing an image within a magnetic resonance imaging system in accordance with an embodiment of the present invention.

DETAILED DESCRIPTION

Figure 1:
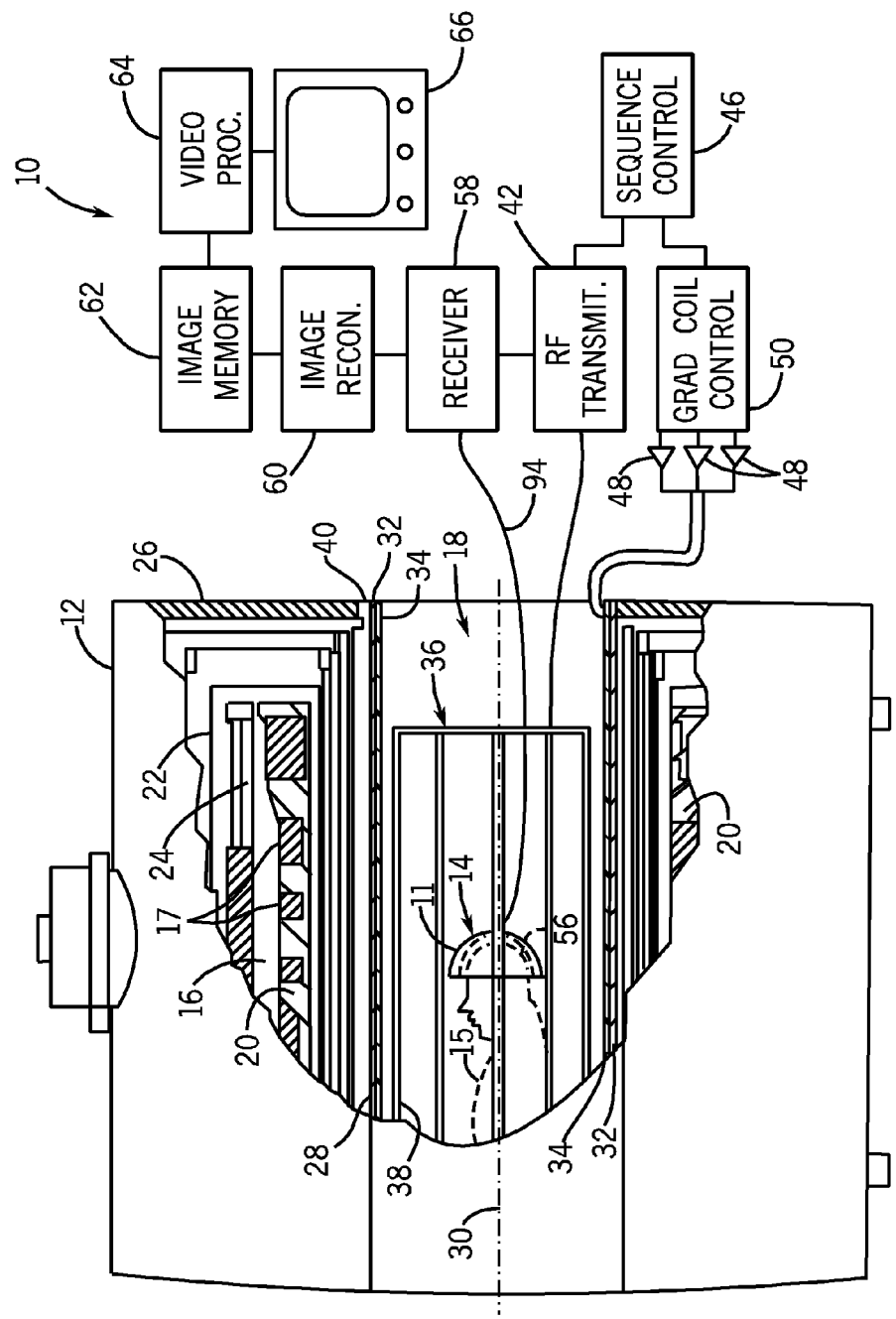
FIG. 1 is a cross-sectional side and block diagrammatic view of a magnetic resonance (MR) imaging system utilizing a dome resonator in accordance with an embodiment of the present invention.

In the following figures the same reference numerals will be used to refer to the same components. While the present invention is described with respect to an apparatus and system for magnetic resonance (MR) and spectroscopy scanning and imaging of a cerebrum, the following apparatus and system is capable of being adapted for various purposes and is not limited to scanning or imaging of a cerebrum or to the following applications: magnetic resonance imaging (MRI) systems, magnetic resonance spectroscopy systems, and other similar applications known in the art.

In the following description, various operating parameters and components are described for one constructed embodiment. These specific parameters and components are included as examples and are not meant to be limiting.

Also, in the following description the term "dome" refers to approximate shape of a device or object. The device or object has a center main portion with a first end and a second end. The center main portion is tapered from the first end to the second end such that the first end is larger in size than the second end. Cross-sectional perimeter of the center main portion may have various shapes, styles, and sizes; the shapes although commonly being elliptical, paraboloidal, symmetrical, or a combination thereof may have other shapes known in the art. The first end and the second end may also be of various shape, style, and size.

Additionally, in the following description the term "surfaces of revolution" refer to perimeter surfaces of a device or object that exist about a center axis. For example, a dome shaped resonator may have a center axis extending between an apex and a center of an aperture opening. Perimeter of the resonator may be paraboloidal in shape and symmetrical about the center axis. Outer or inner surfaces of the resonator may be therefore considered surfaces of revolution about the center axis.

Referring now to FIG. 1, a cross-sectional side and block diagrammatic view of a magnetic resonance (MR) imaging system 10 utilizing a dome resonator 11 in accordance with an embodiment of the present invention is shown. The MRI system 10 includes a static magnet structure 12 (a cylindrical structure) and a signal processing system 13. The signal processing system 13 is coupled to the dome resonator 11 and reconstructs an image for a region of interest 14 of a patient 15 in response to radio frequency magnetic resonance signals, as is further described below.

The static magnet structure 12 includes a superconducting magnet 16 having a plurality of superconducting magnetic field coils 17 which generate a temporally constant magnetic field along a longitudinal axis (z-axis) of a central bore 18 (patient bore). The superconducting magnet coils 17 are supported by a superconducting magnet coil support structure 20 and received in a toroidal helium vessel or can 22.

A main magnetic field shield coil assembly 24 generates a magnetic field that opposes the field generated by the superconducting magnet coils 17. A toroidal vacuum vessel 26 includes a cylindrical member 28 that defines the patient bore 18 and extends parallel to a longitudinal axis 30. On a first exterior side 32 of the cylindrical member 28, which is a longitudinal side farthest away from the axis 30, is a magnetic gradient coil assembly 34.

The patient bore 18 has a RF coil assembly 36 (antennae) mounted therein. The RF coil assembly 36 includes a primary RF coil 38 and a RF shield 40.

The signal processing system 13 includes a RF transmitter 42 that is coupled to a sequence controller 46 and the primary RF coil 38. The RF transmitter 42 is preferably digital. The sequence controller 46 controls a series of current pulse generators 48 via a gradient coil controller 50 that is connected to the magnetic gradient coil assembly 34. The RF transmitter 42 in conjunction with the sequence controller 46 generates a series of spatially located radio frequency signals or encoded magnetic field gradient pulses that are applied across a region of interest 14 within the magnetic field for exciting and manipulating magnetic resonance in selected dipoles of the region of interest 14, such as a portion of a patient 15 within the patient bore 18.

The dome resonator 11 resides within the patient bore 18 and is positioned over a portion of the patient 15. The dome resonator 11 receives the radio frequency magnetic resonance signals emanating from the region of interest 14. In a preferred embodiment of the present invention the dome resonator 11 is positioned over a head 56 of the patient 15 and is utilized to scan a cerebrum of the patient 15.

A radio frequency receiver 58 is connected with the primary RF coil 38 for demodulating magnetic resonance signals emanating from an examined portion of the subject. An image reconstruction apparatus 60 reconstructs the received magnetic resonance signals into an electronic image representation that is stored in an image memory 62. A video processor 64 converts stored electronic images into an appropriate format for display on a video monitor 66.

Figure 2A:
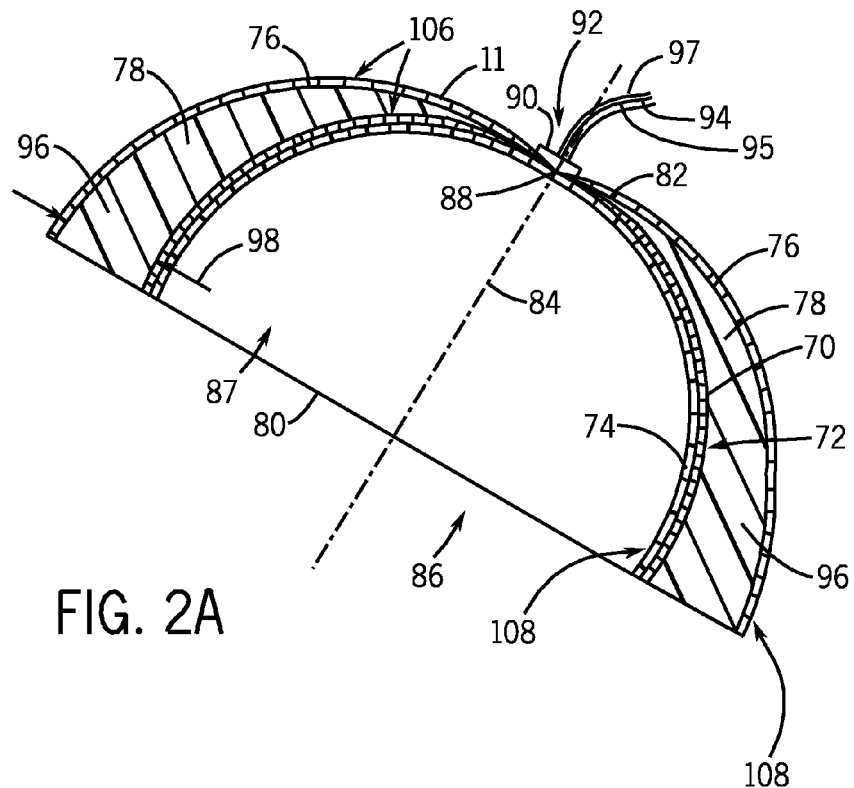
FIG. 2A is a cross-sectional side view of the dome resonator in accordance with an embodiment of the present invention.
Figure 2B:
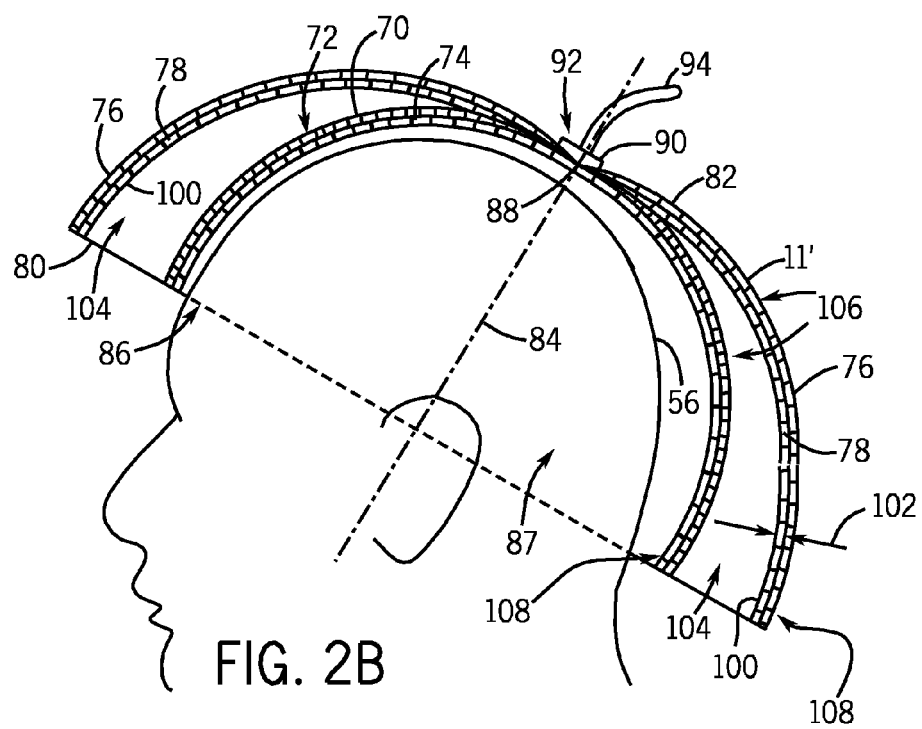
FIG. 2B is a cross-sectional side view of a dome resonator in accordance with another embodiment of the present invention.
Figure 3A:
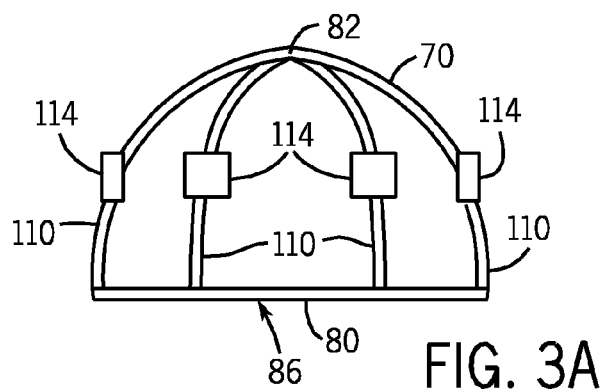
FIG. 3A is a representative side view of a resonator circuit in accordance with an embodiment of the present invention.
Figure 3B:
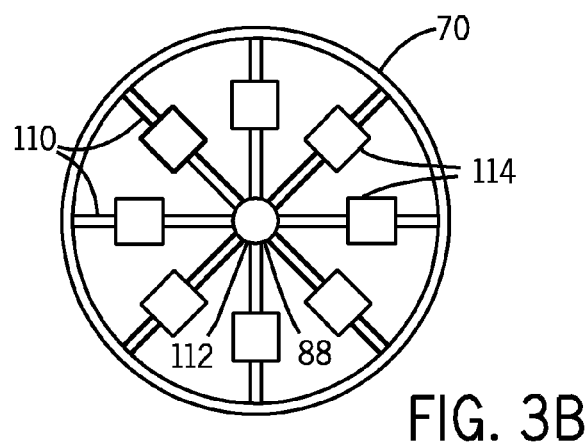
FIG. 3B is a representative bottom view of the resonator circuit in accordance with an embodiment of the present invention.

Referring now to FIGS. 2A and 2B, cross-sectional side views of the dome resonator 11 and of a dome resonator 11", respectively, in accordance with multiple embodiments of the present invention are shown. The dome resonators 11 and 11" are dome shaped and include a resonator circuit 70 that resides on an exterior side 72 of a resonating circuit support 74; the resonator circuit is best seen in FIGS. 3A and 3B and further described below. The circuit support 74 is mechanically fixed to and supports the resonator circuit 70. A shield 76, which is also dome shaped, covers and electrically isolates the resonator circuit 70 from a surrounding environment, which contains objects capable of parasitic electromagnetic coupling to a resonant structure, particularly at high frequencies. The shield 76 of the present invention has additional key aspects and features, which are also described in further detail below. The shield 76 is coupled to an insulating shield support 78 that is coupled to the circuit support 74. The shield support 78, similar to the circuit support 74, provides a rigid supporting member to maintain shape of the shield instead of the resonator circuit 70.

Although, the dome resonators 11 and 11" are shown in paraboloidal configurations they may be in various other geometrical configurations. The dome resonators 11 and 11" may be of various size and shape; they may be elliptical, paraboloidal, or symmetrical in shape, or be in some other known geometrical configuration known in the art that is amendable to providing a uniform magnetic field therein.

The dome resonators 11 and 11" are tapered from a first end 80 to a second end 82 along a center axis 84. The first end 80 has an aperture 86 wherein the head 56 of the patient 15 is inserted into an interior space 87. The second end 82, as shown, converges at an apex 88. An apex connector 90 is coupled within an apex area 92 and serves multiple purposes. A transmission cable 94 is coupled between the resonator 11 and the receiver 58. The transmission cable 94 joins the resonator assembly at connector 90, with the center conductor 95 of the cable 94 joining the resonator circuit 70, and a shield 97 of the cable 94 joining the resonator shield 76. The connector 90 is particularly suited for this, since it is electrically coupled to a virtual ground point (not shown).

The connector 90 may also be used to couple and hold relative positioning of the circuit support 74 to the shield support 78. Of course, the circuit support 74 may be coupled to the shield support 78 using various other methods known in the art. The circuit support 74 may be coupled to the shield support 78 via one or more fasteners (not shown) or adhesives. For example, in FIG. 2A, a shield support 96 is directly adhered over the resonator circuit 70 on to the circuit support 74 and is directly adhered to the shield 76. Width 98 of the shield support 96 decreases in a paraboloidal and uniform manner from the first end 80 to the apex 88. In another example, illustrated by FIG. 2B, a shield support 100 is coupled to the circuit support 74 in the apex area 92 and within the connector 90. The shield support 100 has a uniform width 102 and is separated from the circuit support 74 by an air gap 104. The air gap 104 is largest near the first end 80 and decreases in size, such that distance between the shield support 100 and the circuit support 74 decreases in a paraboloidal and uniform manner from the first end 80 to the apex 88.

The resonator circuit 70 and the shield 76, in the illustrated embodiments of FIGS. 2A and 2B, have respective paraboloidal sections 106 and cylindrical sections 108, the cylindrical sections 108 being parallel to each other. The circuit support 74 and the shield support 78 may be formed of various materials including plastic, fiberglass, resin, polyurethane, lexan, wood, or other rigid insulating material or combination thereof known in the art. In one embodiment of the present invention both the circuit support 74 and the shield support 78 are in the form of supporting laminas.

The shield 76 not only prevents susceptibility to determined frequencies but also provides non-uniform attenuation of radio frequency field strength within the dome resonators 11 and 11". The shield 76 gradually increases amount of attenuation from the first end 80 to the apex 88. The shield 76 preferably tapers uniformly from the first end 80 to the apex 88, such that as distance between the shield 76 and the resonator circuit 70 decreases, attenuation of the field increases. In so doing, the present invention provides a highest amount of attenuation near the apex 88 where field strength, within a conventional dome shaped resonator is typically highest and relative field uniformity is least. The uniformly increasing attenuation characteristic of the shield provides uniform field strength within the resonators 11 and 11". The shield 76 may be formed of various materials including copper, silver, or other non-magnetic conductive materials known in the art. In one embodiment of the present invention copper is used due to its preferred conductive characteristics.

Note a B field from an RF current is effectively shielded by placement of a parallel and oppositely directed current at some point in space. This concept applies in two-dimensions but is widely used as an approximation in three. Generally current, in the dome resonators 11 and 11", does not vary with distance between the shield 76 and the resonator circuit 70, but current density does increase in proportion with increase in field strength as the shield decreases in radius near the apex 88.

Referring now to FIGS. 3A and 3B, representative side and bottom views of the resonator circuit 70 are shown in accordance with a low pass embodiment of the present invention. Although, a low pass embodiment is shown other embodiments will become evident to one skilled in the art, including embodiments, such as a high pass embodiment and a transverse electromagnetic (TEM) embodiment. The resonator circuit 70 includes multiple longitudinal conductive elements 110 that are coupled at the ends 80 and 82 and tapered from the first end 80 to the second end 82. The conductive elements 110 receive the radio frequency magnetic resonance signals that emanate from the region of interest 14. Although, various numbers of longitudinal elements 110 may be used, in the embodiment as shown, an even power of two is used.

Although, the second end 82 is shown in the form of a disc 112, it may be in some other form, such as in the form of a ring, similar to that of the first end 80. The first end 80 and the second end 82 may be in the form of azimuthally directed conductive rings. It is simply preferred that the second end 82 be smaller in size than the first end 80 so that the resonator circuit 70 takes on a dome shape.

The resonator circuit 70 includes multiple capacitive elements, represented by boxes 114, which are coupled in the longitudinal elements 110 and may be coupled in the first end 80 or in the second end 82. The resonator circuit 70 may perform in various configurations, such as in a low pass configuration, a high pass configuration, a hybrid configuration, a TEM configuration, as known in the art.

Figure 4:
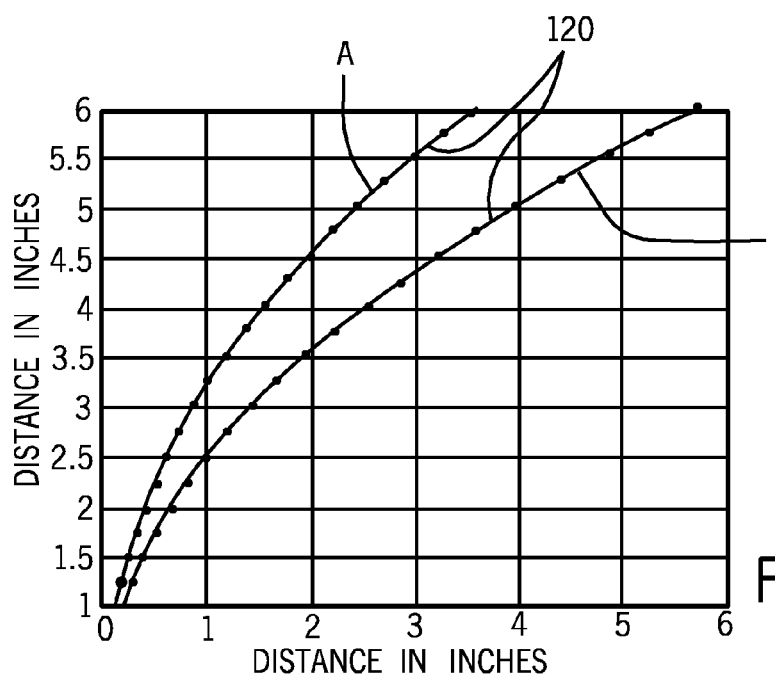
FIG. 4 is a plot of exemplary parabolas for surfaces of revolution in accordance with an embodiment of the present invention.
Figure 6A:
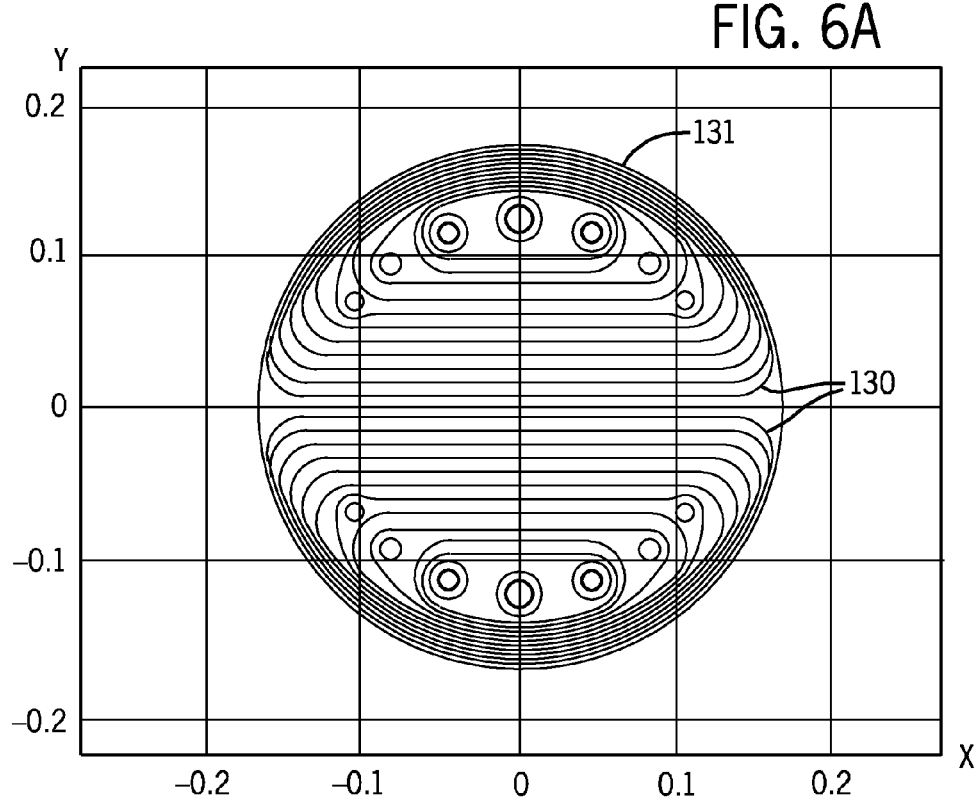
FIG. 6A is an exemplary flux plot for a first section through a paraboloid of revolution, generated from the parabolas of FIG. 4, in accordance with an embodiment of the present invention.
Figure 6B:
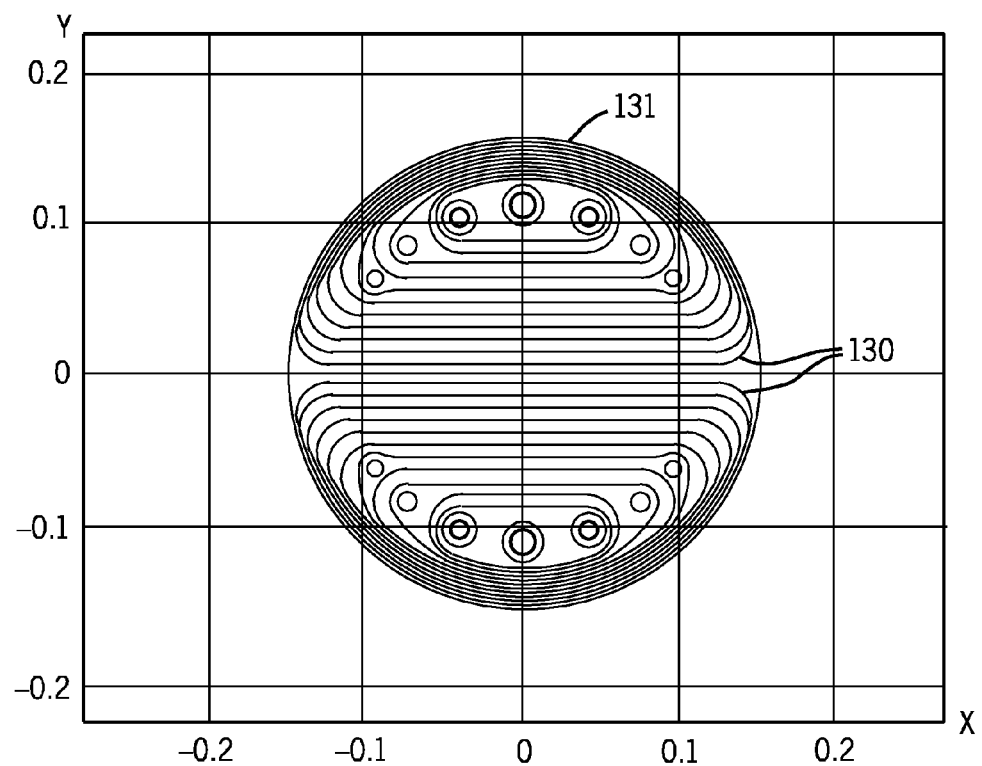
FIG. 6B is an exemplary flux plot for a second section, closer to apex of a resonator of FIG. 6A, through a paraboloid of revolution, generated from the parabolas of FIG. 4, in accordance with an embodiment of the present invention.
Figure 6C:
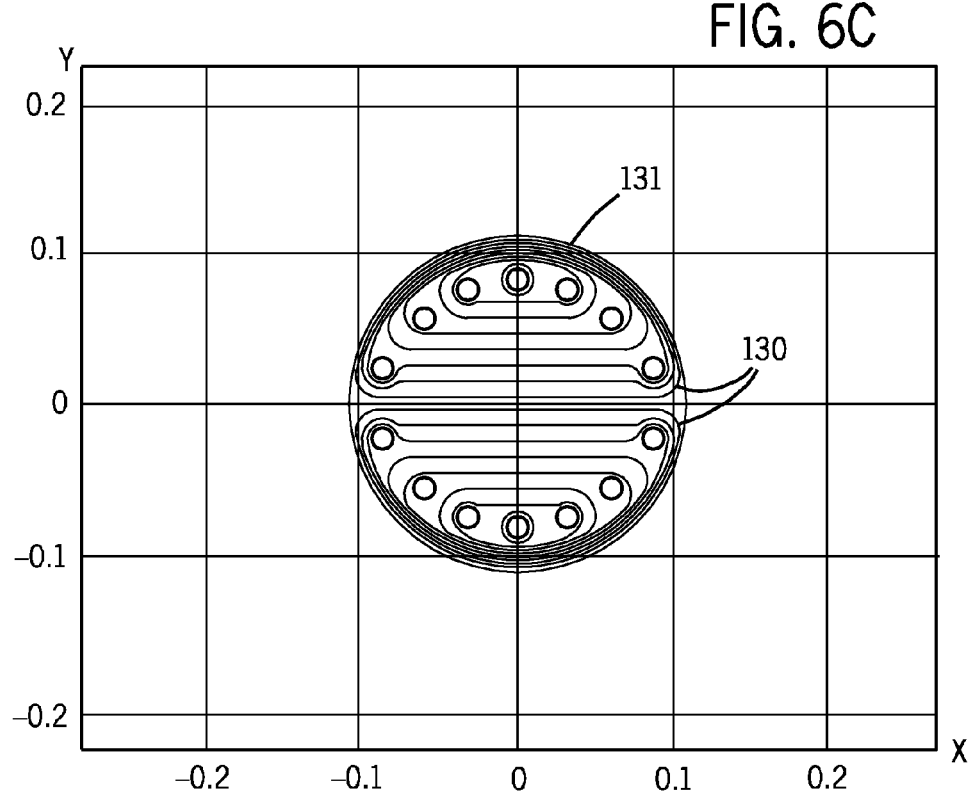
FIG. 6C is an exemplary flux plot for a third section, closer to apex of the resonator than that of FIG. 6B, through a paraboloid of revolution, generated from the parabolas of FIG. 4, in accordance with an embodiment of the present invention.
Figure 6D:
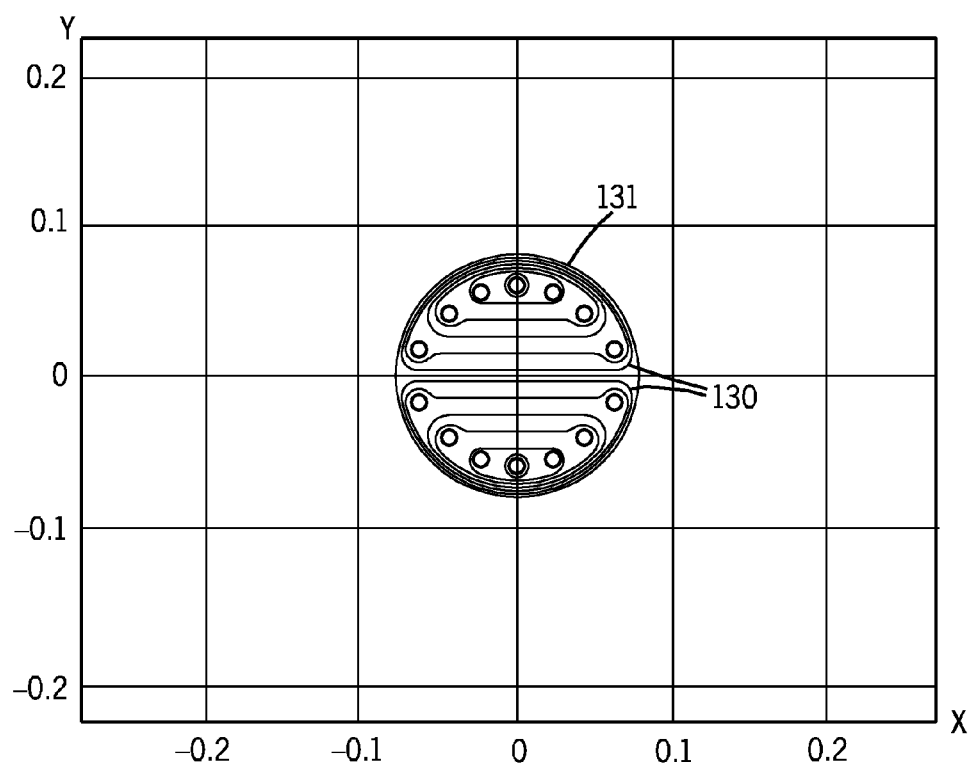
FIG. 6D is an exemplary flux plot for a fourth section, closer to apex of the resonator than that of FIG. 6C, through a paraboloid of revolution, generated from the parabolas of FIG. 4, in accordance with an embodiment of the present invention.

Referring now to FIG. 4, sample plots of exemplary parabolas 120 for surfaces of revolution of the dome resonator 11 in accordance with an embodiment of the present invention are shown. Curve A represents the shield 76 and curve B represents the resonator circuit 70. From the plot relative positioning between shield 76 and the resonator circuit 70 can be determined.

Referring now to FIG. 5, a logic flow diagram illustrating a method of designing and manufacturing the dome resonator 11 in accordance with an embodiment of the present invention is shown.

In step 122, desired performance parameters for the dome resonator 11 are determined. The performance parameters may include items that effect quality and efficiency of image reconstruction, spatial and physical constraints, or patient comfort. The performance parameters may include limitations on resonator dimensions, field uniformity, field flux distribution, and ability to receive determined field strengths and generated frequencies, as well as other performance parameters known in the art.

In step 124, design parameters are determined for the resonator circuit 70 and the shield 76 in response to the determined performance parameters. The design parameters may include a shape configuration, types of materials, material combinations, spacing or distance between the resonator circuit 70 and the shield 76, or other design parameters known in the art. The shape configuration referring to shape of the resonator circuit 70 and the shield 76.

In step 126, a set of exemplary plots, such as the plots shown in FIG. 4, are generated in response to the design parameters. In step 128, a set of flux plots 131 are generated in response to the exemplary plots using conformal mapping techniques known in the art, as shown in FIGS. 6A-6D. Axes x and y in FIGS. 6A-6D correspond with a plane perpendicular to the resonator axis 84 of FIG. 2B. Each flux plot 131 in FIGS. 6A-6D represents a plane section through the resonator 11 or through paraboloids of revolution, generated from the parabolas 120 of FIG. 4. Notice that flux lines 130 are equally spaced illustrating uniform field strength.

In step 132, the flux plots 131 are reviewed to determine whether they satisfy the desired performance parameters. In step 134, when the desired performance parameters are not satisfied the design parameters are adjusted accordingly and the above-stated steps 126-132 are repeated until the desired performance parameters are satisfied. In step 136, the dome resonator 11 is manufactured using the design parameters and dimensions of the resonator circuit 70 and of the shield 76, illustrated in the exemplary plots of step 126. In the current exemplary embodiment, the flux plots are generated by a series of two-dimensional calculations, as an approximation to a three-dimensional calculation; a full three-dimensional calculation may also be performed.

Referring now to FIG. 7, a logic flow diagram illustrating a method of reconstructing an image within the imaging system 10 in accordance with an embodiment of the present invention is shown.

In step 140, a series of magnetic field gradient pulses are generated and applied across the region of interest 14.

In step 142, the resonator circuit 70 is electrically isolated from a surrounding environment, as stated above. In step 144, the shield 76 attenuates field strength within the dome resonator 11. As stated above the shield 76 provides increased attenuation near the second end 82 of the dome resonator 11.

In step 146, the resonator circuit 70 receives radio frequency magnetic resonance signals that emanate from the region of interest 14. In step 148, an image for the region of interest 14 is reconstructed in response to the radio frequency magnetic resonance signals using techniques known in the art.

The above-described steps are meant to be an illustrative example; the steps may be performed synchronously, sequentially, simultaneously, or in a different order depending upon the application.

The present invention provides a shielded dome resonator for a magnetic resonance imaging system that has a shield, which is dome shaped, tapered, and coupled to a resonating circuit in such a manner as to decrease distance between the shield and a resonating circuit, between an aperture side and an apex of the resonating circuit. In so doing, the present invention provides a dome resonator that exhibits a uniform field. The shielded dome resonator of the present invention minimizes generation of artifacts, is efficient, has improved patient comfort, has increased functionality, and is capable of operating in higher field strength and frequency environments.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

The invention claimed is:

1. A dome resonator comprising:
   a resonator circuit exciting or receiving radio frequency magnetic resonance signals in a region of interest and having a plurality of longitudinal conductive elements coupled at a first end and a second end and tapering from said first end to said second end;
   a resonator circuit support coupled to and supporting said resonator circuit; and
   a shield coupled to said resonator circuit support and electrically isolating said resonator circuit from a surrounding environment.

2. A resonator as in claim 1 wherein said resonator circuit excites and receives radio frequency magnetic resonance signals in a region of interest.

3. A resonator as in claim 1 wherein said resonator circuit further comprises a plurality of capacitive elements.

4. A resonator as in claim 1 wherein said second end is in a form of an apex.

5. A resonator as in claim 1 wherein said resonator circuit performs in a configuration selected from at least one of a low pass configuration, a high pass configuration, a hybrid configuration, and a transverse electromagnetic configuration.

6. A resonator as in claim 1 wherein said resonator circuit support is a support lamina.

7. A resonator as in claim 1 wherein said shield prevents susceptibility to determined frequencies.

8. A resonator as in claim 1 wherein said shield is coupled to said resonator circuit support approximately within an apex area.

9. A resonator as in claim 1 wherein said shield is formed of a material selected from at least one copper, silver, and a non-magnetic conductive material.

10. A resonator as in claim 1 wherein said shield is supported by an insulating shield support that is coupled to said resonator circuit support.

11. A resonator as in claim 10 wherein said insulating shield support is coupled to said resonator circuit support approximately within an apex area.

12. A resonator as in claim 10 wherein said insulating shield support is directly coupled over said resonator circuit to said resonator circuit support.

13. A resonator as in claim 10 wherein said insulating shield support is only coupled to said resonator circuit support approximately within an apex area.

14. A resonator as in claim 10 wherein said resonator circuit support and said insulating shield support is formed of a material selected from at least one of plastic, fiberglass, resin, polyurethane, lexan, wood, and a rigid insulating material.

15. A resonator as in claim 1 wherein said shield tapers from said first end to said second end.

16. A resonator as in claim 1 wherein distance between said shield and said resonator circuit decreases from said first end to said second end.

17. A resonator as in claim 1 wherein distance between said shield and said resonator circuit uniformly decreases from said first end to said second end.

18. A resonator as in claim 1 wherein said shield and said resonator circuit have a tapering distance therebetween that is selected to produce a spatially uniform radio-frequency magnetic field within an interior space bounded by said resonator.

19. A resonator as in claim 1 wherein the resonator is in a shape configuration selected from at least one of an ellipsoidal configuration, a paraboloidal configuration, and a symmetrical configuration.

20. A magnetic resonance imaging system comprising:
   a magnet structure having a super conducting magnet generating and applying a series of magnetic field gradient pulses across a region of interest;
   a dome resonator comprising;
   a resonator circuit exciting or receiving radio frequency magnetic resonance signals emanating from said region of interest and having a plurality of longitudinal conductive elements coupled at a first end and a second end and tapering from said first end to said second end;
   a resonator circuit support coupled to and supporting said resonator circuit; and
   a shield coupled to said resonator circuit support and electrically isolating said resonator circuit from a surrounding environment; and
   a signal processing system coupled to said dome resonator and reconstructing an image for said region of interest in response to said radio frequency magnetic resonance signals.

21. A method of reconstructing an image within a magnetic resonance imaging system having a dome resonator comprising:
   generating and applying a series of magnetic field gradient pulses across a region of interest;
   electrically isolating said resonator circuit from a surrounding environment;
   attenuating field strength within the dome resonator via a shield;
   receiving radio frequency magnetic resonance signals emanating from said region of interest via a resonator circuit of the dome resonator; and
   reconstructing an image for said region of interest in response to said radio frequency magnetic resonance signals.

* * * * *